(12) United States Patent
Nishizato et al.

(10) Patent No.: US 10,138,555 B2
(45) Date of Patent: Nov. 27, 2018

(54) GAS CONTROL SYSTEM AND PROGRAM FOR GAS CONTROL SYSTEM

(71) Applicant: HORIBA STEC, CO., LTD., Kyoto (JP)

(72) Inventors: Hiroshi Nishizato, Kyoto (JP); Kotaro Takijiri, Kyoto (JP); Masakazu Minami, Kyoto (JP); Atsuko Teraoka, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 217 days.

(21) Appl. No.: 15/291,264

(22) Filed: Oct. 12, 2016

(65) Prior Publication Data

US 2017/0101715 A1    Apr. 13, 2017

(30) Foreign Application Priority Data

Oct. 13, 2015  (JP) .................. 2015-202481

(51) Int. Cl.
*C23C 16/448* (2006.01)
*C23C 16/52* (2006.01)
(Continued)

(52) U.S. Cl.
CPC .......... *C23C 16/52* (2013.01); *C23C 16/4481* (2013.01); *C23C 16/4482* (2013.01); *G01N 21/3504* (2013.01); *G01N 21/84* (2013.01); *G01N 33/0004* (2013.01); *G05D 11/00* (2013.01); *G01N 2021/8411* (2013.01); *G01N 2021/8578* (2013.01); *Y10T 137/0329* (2015.04); *Y10T 137/2499* (2015.04); *Y10T 137/2509* (2015.04)

(58) Field of Classification Search
CPC ......... Y10T 137/2499; Y10T 137/2509; Y10T 137/0329; C23C 16/4481; C23C 16/4482
See application file for complete search history.

(56) References Cited

U.S. PATENT DOCUMENTS 5,262,356 A  *  11/1993  Fujii ..................... C23C 16/401
                                                    118/715
6,772,781 B2 *  8/2004  Doty .................... G05D 11/132
                                                    137/597

(Continued)

FOREIGN PATENT DOCUMENTS

JP          2004-363271          12/2004

*Primary Examiner* — Kevin Murphy
(74) *Attorney, Agent, or Firm* — Greenblum & Bernstein, P.L.C.

(57) ABSTRACT

A gas control system includes: a first valve that is provided in a carrier gas line or in a gas supply line; a flow rate control mechanism that is provided in a diluent gas line and includes a flow rate sensor and a second valve; a contactless type first concentration sensor; a first valve control part; a diluent gas setting flow rate calculation part adapted to, on the basis of a preset setting total flow rate of a post-dilution mixed gas and a post-dilution measured concentration, calculate a diluent gas setting flow rate that is a flow rate of a diluent gas to be flowed through the diluent gas line; and a second valve control part adapted to control the opening level of the second valve so as to decrease the deviation between the diluent gas setting flow rate and a measured flow rate measured by the flow rate sensor.

7 Claims, 7 Drawing Sheets

(51) Int. Cl.
*G01N 21/3504* (2014.01)
*G01N 21/84* (2006.01)
*G01N 33/00* (2006.01)
*G05D 11/00* (2006.01)
*G01N 21/85* (2006.01)

(56) References Cited

U.S. PATENT DOCUMENTS

| | | | | |
|---|---|---|---|---|
| 7,438,079 | B2* | 10/2008 | Cohen | B01F 3/028 |
| | | | | 137/3 |
| 8,091,575 | B2* | 1/2012 | Gammon | G05D 11/132 |
| | | | | 137/100 |
| 8,459,290 | B2* | 6/2013 | Minami | G05D 11/132 |
| | | | | 118/689 |
| 8,931,512 | B2* | 1/2015 | Cruse | B01F 3/028 |
| | | | | 137/597 |
| 2014/0020764 | A1* | 1/2014 | Woelk | C30B 25/14 |
| | | | | 137/1 |
| 2015/0068613 | A1* | 3/2015 | Taskar | G05D 7/0641 |
| | | | | 137/88 |

* cited by examiner

US 10,138,555 B2

GAS CONTROL SYSTEM AND PROGRAM FOR GAS CONTROL SYSTEM

TECHNICAL FIELD

The present invention relates to a gas control system used to supply a mixed gas containing a material gas, which is produced by vaporizing a material, at a predetermined concentration and flow rate.

BACKGROUND ART

For example, when manufacturing a semiconductor, it is required to supply a mixed gas containing a material gas, which is produced by vaporizing a liquid or solid material, into a deposition apparatus at a predetermined concentration and flow rate.

The material gas is produced by introducing a carrier gas into the material stored in a tank to, for example, bubble the material for the vaporization. The material gas produced by the vaporization in the tank is mixed with the carrier gas to produce the mixed gas, and the mixed gas flows through a gas supply line connected from the tank to the deposition apparatus. The concentration and flow rate of the mixed gas are conventionally controlled to predetermined values by a gas control system that is provided in the gas supply line and includes a concentration sensor and a mass flow controller (see Patent Literature 1).

CITATION LIST

Patent Literature

Patent Literature 1: Japanese Unexamined Patent Publication JP-A 2004-363271

SUMMARY OF INVENTION

Technical Problem

However, in the case where the mass flow controller is provided in the gas supply line, when the gas supply line near the tank is placed in a high temperature environment in order to facilitate the vaporization of the material, or when the reactivity of the material gas is high, it is difficult for a flow rate sensor of the mass flow controller provided in the gas supply line to accurately measure the flow rate of the mixed gas. This is because the high temperature environment makes it difficult to form a temperature difference for measuring the flow rate using, for example, a thermal type flow rate sensor, or the material gas having high reactivity corrodes a sensor mechanism of the flow rate sensor. As a result, the mixed gas having the predetermined concentration and flow rate is not sometimes supplied to the deposition apparatus to cause a variation in film thickness or film composition.

Also, in the case where the concentration sensor adapted to directly measure the total pressure of the mixed gas and the partial pressure of the material gas and thereby measure the concentration of the material gas of the mixed gas is provided in the gas supply line, the same problem may occur.

The present invention is made in consideration of the above-described problems, and intends to provide a gas control system capable of supplying a mixed gas at a predetermined concentration and flow rate even when a material gas produced by vaporization is at high temperature or highly reactive, and a program for the gas control system.

Solution to Problem

That is, the present invention is a gas control system used for a vaporizer including: a tank adapted to contain a material; a carrier gas line adapted to introduce a carrier gas into the tank; a gas supply line through which a material gas produced by vaporizing the material and led out of the tank and the carrier gas flow; and a diluent gas line adapted to merge with the gas supply line and introduce a diluent gas into the gas supply line. Also, the gas control system includes: a first valve that is provided in the carrier gas line or provided in the gas supply line on an upstream side of a merging point with the diluent gas line; a flow rate control mechanism that is provided in the diluent gas line and includes a flow rate sensor and a second valve; a first concentration sensor that is provided in the gas supply line on a downstream side of the merging point with the diluent gas line and adapted to measure the concentration of the material gas in a post-dilution mixed gas containing the material gas, the carrier gas, and the diluent gas; a first valve control part adapted to control the opening level of the first valve so as to decrease the deviation between the preset setting concentration of the material gas in the post-dilution mixed gas and the post-dilution measured concentration of the material gas in the post-dilution mixed gas measured by the first concentration sensor; a diluent gas setting flow rate calculation part adapted to, on the basis of the preset setting total flow rate of the post-dilution mixed gas, the post-dilution measured concentration, and the estimated or actually measured concentration of the material gas in a pre-dilution mixed gas, calculate a diluent gas setting flow rate that is the flow rate of the diluent gas to be flowed through the diluent gas line; and a second valve control part adapted to control the opening level of the second valve so as to decrease the deviation between the diluent gas setting flow rate and a measured flow rate measured by the flow rate sensor.

Such a gas control system makes it possible to prevent a sensor for directly contacting with the material gas to measure a flow rate or a concentration from being provided in the gas supply line. Accordingly, even when the material gas is at high temperature or highly reactive, the sensor is essentially never adversely affected by the material gas. Further, droplets produced by the reliquefaction of the material gas and/or particles produced by the thermal decomposition of the material are never attached to the sensor in principle. In other words, the droplets and/or the particles never impede a flow rate or concentration control operation.

On the other hand, since the first concentration sensor is provided in the gas supply line on the downstream side of the merging point with the diluent gas line, even when the pre-dilution mixed gas is at high temperature or highly reactive, the pre-dilution mixed gas can be sufficiently cooled by or diluted with the diluent gas. Accordingly, a reduction in measurement accuracy of the first concentration sensor due to the effect of heat and the deterioration of a sensor mechanism of the first concentration sensor are unlikely to occur. In addition, the flow rate sensor provided in the diluent gas line also measures only the diluent gas, and therefore the flow rate sensor is not affected by the material gas and can therefore keep accurate measurement over a long term.

Further, the concentration of the post-dilution mixed gas is controlled with the first valve, and the flow rate of the post-dilution mixed gas is independently controlled by controlling the flow rate of the diluent gas with the second valve so as to meet the setting total flow rate. That is, the flow rate and concentration of the post-dilution mixed gas can be simultaneously independently controlled.

As described, since the post-dilution measured concentration measured by the first concentration sensor and the measured flow rate measured by the flow rate sensor constantly have accurate values, and on the basis of the accurate measured values, the flow rate and concentration of the post-dilution mixed gas can be independently controlled, the post-dilution mixed gas having a desired flow rate or concentration can be stably obtained over a long term. Accordingly, for example, it becomes possible to eliminate a variation in film thickness or film composition in a deposition apparatus and therefore constantly manufacture a semiconductor of the same quality.

In order to make it possible to accurately measure the post-dilution measured concentration of the material without contact with the post-dilution mixed gas and simply provide the first concentration sensor in the gas supply line, it is only necessary that the first concentration sensor is an infrared absorption type concentration sensor.

In order to make it possible to accurately control both of the total flow rate of the post-dilution mixed gas and the concentration of the material gas, it is only necessary that the gas control system further includes a contactless type second concentration sensor that is provided in the gas supply line on the upstream side of the merging point with the diluent gas line and adapted to measure the concentration of the material gas in the pre-dilution mixed gas containing the material gas and the carrier gas, in which the diluent gas setting flow rate calculation part is configured to calculate the diluent gas setting flow rate on the basis of the setting total flow rate, the post-dilution measured concentration, and the pre-dilution measured concentration of the material gas in the pre-dilution mixed gas measured by the second concentration sensor.

In order to continuously keep the concentration of the material gas in the post-dilution mixed gas at the setting concentration, it is only necessary that the first valve control part is configured to, when the post-dilution measured concentration is larger than the setting concentration, change an opening level in a direction to close the first valve, and when the post-dilution measured concentration is smaller than the setting concentration, change the opening level in a direction to open the first valve.

In order to make it possible to independently control the amount of the material gas produced in the tank as well, and control the concentration of the material gas in the post-dilution mixed gas with high responsiveness while keeping the total flow rate of the post-dilution mixed gas at the setting total flow rate, it is only necessary that the gas control system further includes: a third valve that is provided in the carrier gas line; a pressure sensor that is provided in the tank and adapted to measure the pressure of the inside of the tank; and a third valve control part adapted to control the opening level of the third valve so as to decrease the deviation between a preset setting pressure and a measured pressure measured by the pressure sensor.

Specific configurations for making it possible to uniformly introduce the post-dilution mixed gas into a chamber of a semiconductor manufacturing apparatus such as a deposition apparatus from multiple introduction ports at the same flow rate or concentration include one in which multiple parallel branch gas supply lines are provided from the tank and diluent gas lines respectively individually merge with the gas supply lines; the gas supply lines are respectively individually provided with first valves and first concentration sensors; and the diluent gas lines are respectively individually provided with flow rate control mechanisms can be cited.

In order to make it possible for an existing gas control system to obtain the same effects as those of the present invention, it is only necessary to install a program as described below in the existing gas control system. That is, it is only necessary that the program is a program for a gas control system used for a vaporizer including: a tank adapted to contain a material; a carrier gas line adapted to introduce a carrier gas into the tank; a gas supply line through which a material gas produced by vaporizing the material and led out of the tank and the carrier gas flow; and a diluent gas line adapted to merge with the gas supply line and introduce a diluent gas into the gas supply line. Also, it is only necessary that the gas control system is one including: a first valve that is provided in the carrier gas line or provided in the gas supply line on an upstream side of a merging point with the diluent gas line; a flow rate control mechanism that is provided in the diluent gas line and includes a flow rate sensor and a second valve; and a first concentration sensor that is provided in the gas supply line on a downstream side of the merging point with the diluent gas line and adapted to measure the concentration of the material gas in a post-dilution mixed gas containing the material gas, the carrier gas, and the diluent gas. Further, it is only necessary that the program is one instructing a computer to fulfill functions as: a first valve control part adapted to control the opening level of the first valve so as to decrease the deviation between the preset setting concentration of the material gas in the post-dilution mixed gas and the post-dilution measured concentration of the material gas in the post-dilution mixed gas measured by the first concentration sensor; a diluent gas setting flow rate calculation part adapted to, on the basis of the preset setting total flow rate of the post-dilution mixed gas, the post-dilution measured concentration, and the estimated or actually measured concentration of the material gas in a pre-dilution mixed gas, calculate a diluent gas setting flow rate that is the flow rate of the diluent gas to be flowed through the diluent gas line; and a second valve control part adapted to control the opening level of the second valve so as to decrease the deviation between the diluent gas setting flow rate and a measured flow rate measured by the flow rate sensor.

The program for the gas control system as described above may be one adapted to be electronically delivered or one adapted to be stored in a storage medium such as a CD, DVD, or flash memory.

Advantageous Effects of Invention

Since the gas control system of the present invention does not have any measurement mechanism for measuring a flow rate or a concentration in the gas supply line as described, there is no chance in principle that a sensor is affected by high temperature or by corrosion due to the material gas to cause a measurement error. Also, a measurement error due to the attachment of droplets produced by the reliquefaction of the material gas and/or the attachment of particles to the measurement mechanism does not occur. Accordingly, the gas control system of the present invention is unlikely to temporally change, and therefore makes it possible to, over a long term, continuously supply the post-dilution mixed gas accurately kept at the setting total flow rate or the setting concentration.

DESCRIPTION OF EMBODIMENTS

A gas control system 200 according to a first embodiment of the present invention will be described with reference to each drawing.

Figure 1:
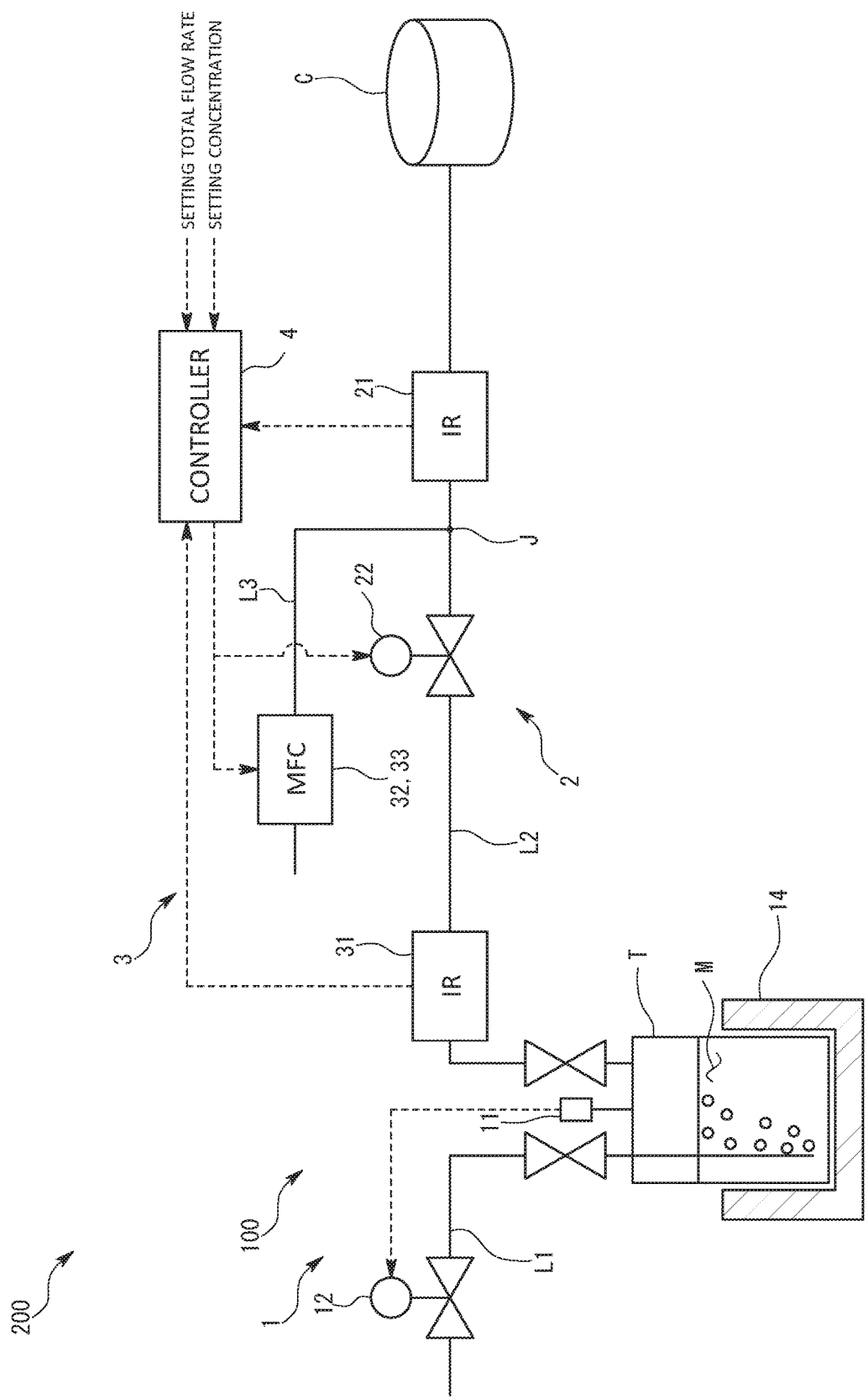
FIG. 1 is a schematic diagram illustrating a gas control system according to a first embodiment of the present invention.

The gas control system 200 illustrated in FIG. 1 is one used to supply a mixed gas into a chamber of a semiconductor manufacturing apparatus such as a deposition apparatus at a predetermined setting total flow rate and setting concentration. More specifically, the gas control system 200 is one used for a vaporizer 100 adapted to bubble a liquid material M using a carrier gas to produce a material gas.

The vaporizer 100 is configured to include: a tank T; a carrier gas line L1 inserted into the tank T; a gas supply line L2 led out from inside the tank T; and a diluent gas line L3 merging with the gas supply line L2.

The tank T is one adapted to contain the liquid material M. The material M is a semiconductor material such as trimethyl gallium $(Ga(CH_3)_3)$. When temperature is reduced or pressure is increased after the material M has been vaporized to produce the material gas, the material gas may be reliquefied. Around the tank T, a heater is provided, and the material gas is adapted to be produced at a desired saturated vapor pressure by appropriately controlling the temperature of the material M using the heater.

The carrier gas line L1 is an introduction pipe for introducing the carrier gas containing an inert gas such as nitrogen or helium, and the like into the tank T to bubble the material M. The carrier gas line L1 is configured such that the fore end part thereof is opened near the bottom surface inside the tank T to make carrier gas bubbles rise from the bottom side of the liquid material M to the liquid surface.

The gas supply line L2 is a lead-out pipe connecting from the inside of the tank T to the chamber. Through the gas supply line L2, the mixed gas containing at least the material gas and the carrier gas flows.

The diluent gas line L3 is a pipe for introducing a diluent gas into the gas supply line L2. In the first embodiment, the diluent gas is prepared having the same composition as that of the carrier gas, but may have a different composition. The concentration or composition of the mixed gas is changed between before and after the merging point J of the diluent gas line L3 with the gas supply line L2. That is, on the upstream side of the merging point J in the gas supply line L2, a pre-dilution mixed gas containing only the carrier gas and the material gas flows. On the other hand, on the downstream side of the merging point J in the gas supply line L2, a post-dilution mixed gas containing the carrier gas, the material gas, and the diluent gas flows.

Further, the gas control system 200 includes: fluidic devices provided in respective parts of the vaporizer 100 configured as described above; and a controller 4 adapted to monitor or control the respective fluidic devices. The fluidic devices include various types of sensors and valves, and the controller 4 is a so-called computer including some components such as a CPU, A/D and D/A converters, and input/output means. The controller 4 is one that partially provides functions of the gas control system 200 by executing a program for the gas control system stored in the memory to cooperate with the respective devices.

More specifically, the gas control system 200 is configured to include: a material gas control mechanism 1 adapted to control a producing state of the material gas in the tank T; a concentration control mechanism 2 adapted to control the concentration of the material gas in the mixed gas flowing through the gas supply line L2; and a dilution control mechanism 3 adapted to control a dilution state of the mixed flowing through the gas supply line L2.

The respective parts will be described.

Figure 2:
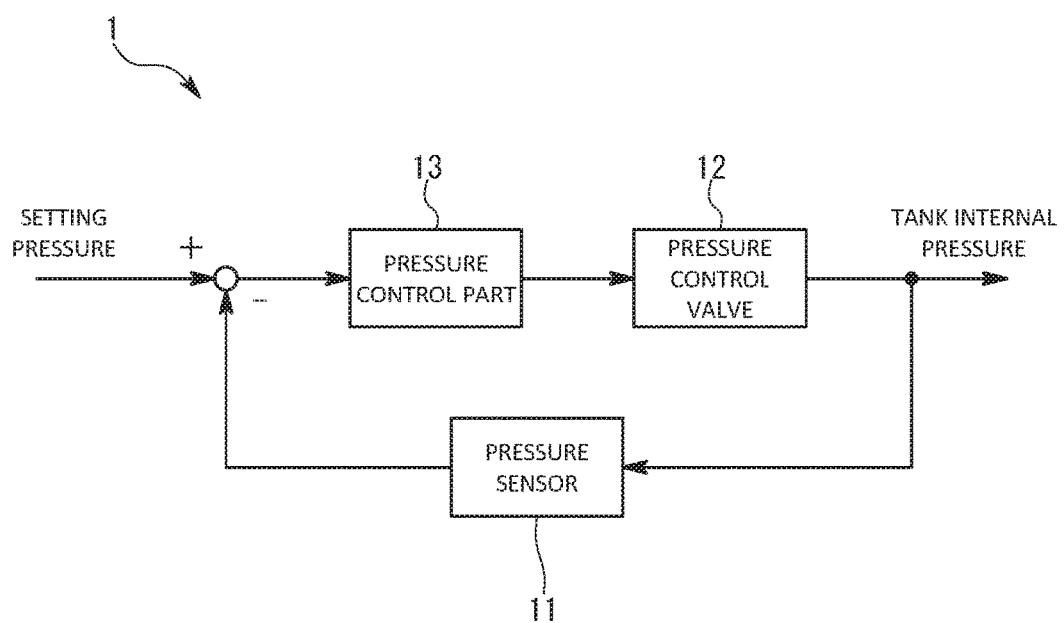
FIG. 2 is a schematic control block diagram illustrating the configuration of a material gas control mechanism in the gas control system of the first embodiment.

As illustrated in a control block diagram of FIG. 2, the material gas control mechanism 1 is one adapted to control the amount of the material gas produced from inside the tank T by controlling the pressure and temperature of the inside of the tank T. That is, the material gas control mechanism 1 includes a pressure sensor 11, pressure control valve 12, pressure control part 13, and temperature controller 14. Note that the pressure control valve 12 corresponds to a third valve in claims, and the pressure control part 13 corresponds to a third valve control part in the claims.

The pressure sensor 11 is one provided so as to communicatively connect to a hollow part inside the tank T and adapted to measure the pressure of the gas inside the tank T.

The pressure control valve 12 is provided in the carrier gas line L1. By changing the opening level of the pressure control valve 12, the inflow amount of the carrier gas into the tank T is regulated to keep the pressure inside the tank T constant.

The pressure control part 13 is one adapted to control the opening level of the pressure control valve 12 so as to decrease the deviation between a preset setting pressure and a measured pressure measured by the pressure sensor 11. The pressure control part 13 is one adapted to provide a function thereof by executing the program in the controller 4. As illustrated in, for example, the control block diagram of FIG. 2, the pressure control part 13 is configured as a controller for pressure feedback control.

The temperature controller 14 is a heater adapted to heat the material M inside the tank T so as to keep the temperature of the material M constant at a preset setting temperature.

Since the material gas control mechanism 1 keeps the pressure and temperature inside the tank T constant as described, the production amount of the material gas is kept within a predetermined allowable range.

The concentration control mechanism 2 is one including a first concentration sensor 21, concentration control valve 22, and concentration control part 23. The concentration control mechanism 2 and the below-described dilution control mechanism 3 affect each other, and as illustrated in a control block diagram of FIG. 3, the concentration control mechanism 2 constitutes a one-input one-output concentration control system with the setting concentration as the input and the concentration of the material gas in the post-dilution mixed gas as the output. Note that the concentration control valve 22 corresponds to a first valve in the claims, and the concentration control part 23 corresponds to a first valve control part.

The first concentration sensor 21 is one provided in the gas supply line L2 on the downstream side of the merging point J with the diluent gas line L3, and adapted to measure the concentration of the material gas in the post-dilution mixed gas containing the material gas, the carrier gas, and the diluent gas. The first concentration sensor 21 is a contactless type sensor, and measures the concentration of the material gas without direct contact of a sensor mechanism thereof with the post-dilution mixed gas. For example, the first concentration sensor 21 is an NDIR (Non-Dispersive InfraRed) type sensor, and adapted to make infrared light incident through a transmission window formed in the gas supply line L2 pipe, and measure absorptance from infrared light having passing through the post-dilution mixed gas to convert the absorptance to the concentration of the material gas. Since the first concentration sensor 21 is configured so as to avoid contact with the post-dilution mixed gas as described, a reduction in measurement accuracy due to the attachment of droplets produced by the reliquefaction of the material gas and/or the attachment of particles produced by the thermal decomposition of the material M is unlikely to occur. In addition, describing the contactless type concentration sensor in another way, it can also be described that, for example, the concentration sensor is configured such that an irradiator adapted to irradiate the material gas with light, a sound wave, a radio wave, or the like or a detector adapted to detect light, a sound wave, a radio wave, or the like does not directly contact with the material gas.

The concentration control valve 22 is provided in the gas supply line L2 on the upstream side of the merging point J with the diluent gas line L3, and on the downstream side of the below-described second concentration sensor 31. That is, the concentration control valve 22 is arranged on the downstream side in a flow path from the tank T to the merging point J. Note that the opening level of the concentration control valve 22 and the flow rate of the pre-dilution mixed gas passing through the concentration control valve 22 have a proportional relationship or a positive correlation.

The concentration control part 23 is configured to control the opening level of the concentration control valve 22 so as to decrease the deviation between the setting concentration of the material gas in the post-dilution mixed gas, which is preliminarily set through an input/output mechanism of the controller 4, and the post-dilution measured concentration of the material gas in the post-dilution mixed gas, which is measured by the first concentration sensor 21. That is, the concentration control part 23 is configured to control the opening level of the concentration control valve 22 using as a feedback value a value obtained by multiplying the deviation between the setting concentration and the post-dilution measured concentration by a preset gain. More specifically, the concentration control part 23 is configured to, when the post-dilution measured concentration is larger than the setting concentration, change the opening level in a direction to close the concentration control valve 22, and when the post-dilution measured concentration is smaller than the setting concentration, change the opening level in a direction to open the concentration control valve 22.

Figure 3:
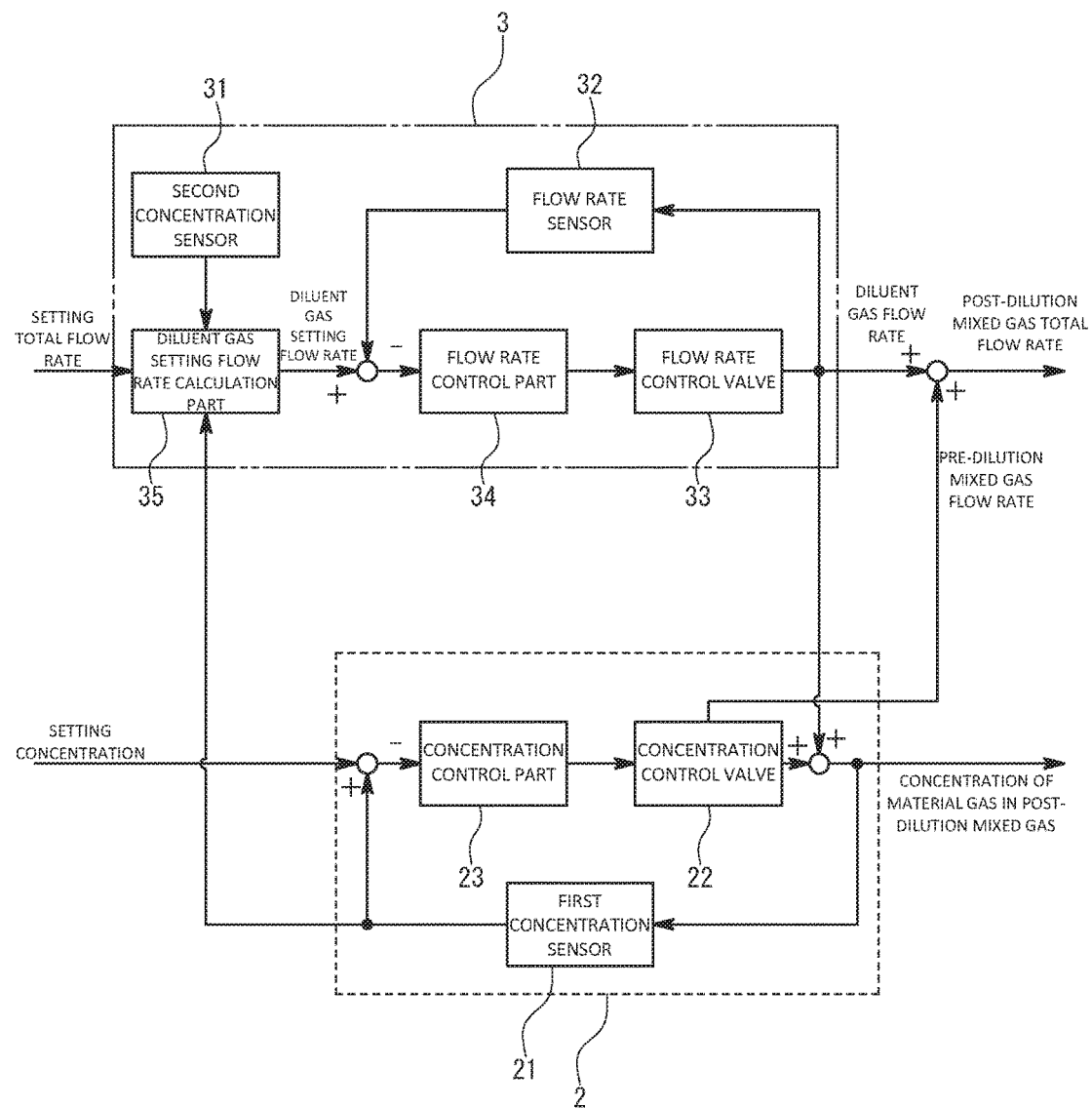
FIG. 3 is a schematic control block diagram illustrating the configurations of a concentration control mechanism and dilution control mechanism in the gas control system of the first embodiment.

When viewed as the concentration control system as illustrated in the control block diagram of FIG. 3, the concentration control mechanism 2 configured as described operates so as to keep the post-dilution measured concentration constant at the setting concentration even though the flow rate of the diluent gas is inputted as disturbance.

The dilution control mechanism 3 is configured to include: the second concentration sensor 31 that is provided in the gas supply line L2; a mass flow controller MFC that is provided in the diluent gas line L3; and a diluent gas setting flow rate calculation part 35 adapted to set a diluent gas setting flow rate for the mass flow controller MFC. The dilution control mechanism 3 is one adapted to dilute the pre-dilution mixed gas so as to make the total flow rate of the post-dilution mixed gas equal to the preset setting total flow rate. As illustrated in the control block diagram of FIG. 3, the dilution control mechanism 3 constitutes a one-input one-output flow rate control system adapted to input the setting total flow rate and output the total flow rate of the post-dilution mixed gas or a one-input one-output flow rate control system adapted to input the diluent gas setting flow rate and output the measured flow rate of the diluent gas.

The second concentration sensor 31 is provided in the gas supply line L2 near the tank T. That is, the second concentration sensor 31 is arranged in the gas supply line L2 on the upstream side of the concentration control valve 22. The second concentration sensor 31 is one adapted to measure the concentration of the material gas in the pre-dilution mixed gas without direct contact with the pre-dilution mixed gas in the same manner as the first concentration sensor 21. The second concentration sensor 31 is also unlikely to be affected by droplets produced by the reliquefaction of the material gas and/or particles.

The mass flow controller MFC is a flow rate control mechanism including a flow rate sensor 32, flow rate control valve 33, and flow rate control part 34, which are packaged so as to form one unit. From direct perspective, the mass flow controller MFC is one adapted to control the flow rate of the diluent gas flowing through the diluent gas line L3. On the other hand, from indirect perspective, the mass flow controller MFC is also one adapted to control the flow rate of the post-dilution mixed gas by controlling the flow rate of the diluent gas. Note that the flow rate control valve 33 corresponds to a second valve in the claims, and the flow rate control part 34 corresponds to a second valve control part in the claims.

Since the material gas does not flow through the diluent gas line L3, droplets produced by the reliquefaction of the material gas and/or particles produced by the thermal decomposition of the material gas are never attached to the flow rate sensor 32. Accordingly, the measurement accuracy of the flow rate sensor 32 is unlikely to be reduced even after long-term use.

The flow rate control part 34 is one adapted to control the opening level of the flow rate control valve 33 so as to decrease the deviation between the diluent gas setting flow rate set from outside the mass flow controller MFC and the diluent gas measured flow rate measured by the flow rate sensor 32. That is, as illustrated in the control block diagram of FIG. 3, in the feedback control system for the flow rate of the diluent gas, the flow rate control part 34 is configured to fulfill a function as a flow rate controller for the diluent gas. For example, the flow rate control part 34 is adapted to control the opening level of the flow rate control valve 33 using as a feedback value a value obtained by multiplying the flow rate deviation of the diluent gas by a predetermined gain.

The diluent gas setting flow rate calculation part 35 is one adapted to set the diluent gas setting flow rate as a target value for the flow rate control part 34 of the mass flow controller MFC. More specifically, the diluent gas setting flow rate calculation part 35 is configured to calculate the diluent gas setting flow rate on the basis of the preset setting total flow rate, the post-dilution measured concentration measured by the first concentration sensor 21, and the pre-dilution measured concentration measured by the second concentration sensor 31.

That is, from the post-dilution measured concentration of the moment and the pre-dilution measured concentration of the moment, the diluent gas setting flow rate calculation part 35 calculates the flow rate of the diluent gas required to achieve the setting total flow rate. Then, the diluent gas setting flow rate calculation part 35 sets the calculated flow rate for the flow rate control part 34 as the diluent gas setting flow rate. In addition, the diluent gas setting flow rate is calculated on the basis of the below-described calculation expression.

First, the post-dilution measured concentration measured by the first concentration sensor 21 can be expressed as in Expression (1) from the definition of concentration.

[Expression 1]

$$IR_{OUT} = Q_{VAP}/Q_{TOTAL} \quad (1)$$

Here, $IR_{OUT}$: the post-dilution measured concentration, $Q_{VAP}$: the flow rate of the material gas, and $Q_{TOTAL}$: the flow rate of the post-dilution mixed gas.

In addition, the pre-dilution measured concentration measured by the second concentration sensor. 31 can also be expressed as in Expression (2).

[Expression 2]

$$IR_{IN} = Q_{VAP}/Q_{VAP} + Q_{CAR} \quad (2)$$

Here, $IR_{IN}$: the pre-dilution measured concentration, and $Q_{CAR}$: the flow rate of the carrier gas. Accordingly, ($Q_{VAP} + Q_{CAR}$) is the flow rate of the pre-dilution mixed gas.

Also, the flow rate of the post-dilution mix gas can be expressed as in Expression (3).

[Expression 3]

$$Q_{TOTAL} = Q_{VAP} + Q_{CAR} + Q_{DIL} \quad (3)$$

Here, $Q_{DIL}$: the flow rate of the diluent gas.

On the basis of Expressions (1) to (3), the flow rate $Q_{DIL}$ of the diluent gas can be expressed as in Expression (4) using the post-dilution measured concentration $IR_{OUT}$, the pre-dilution measured concentration $IR_{IN}$, and the flow rate $Q_{TOTAL}$ of the post-dilution mixed gas.

[Expression 4]

$$Q_{DIL}(1 - IR_{OUT}/IR_{IN})Q_{TOTAL} \quad (4)$$

Accordingly, it turns out that in order to make the flow rate $Q_{TOTAL}$ of the post-dilution mixed gas equal to the setting total flow rate, it is only necessary to, as the diluent gas setting flow rate, set the flow rate $Q_{DIL}$ of the diluent gas calculated using Expression (4). As described, the diluent gas setting flow rate calculation part 35 calculated the diluent gas setting flow rate on the basis of Expression (4) and sets the calculated diluent gas setting flow rate for the flow rate control part 34. In other wording, the diluent gas setting flow rate calculation part 35 is configured to, as in Expression (4), calculate the ratio of the diluent gas to the post-dilution mixed gas from the concentration of the pre-dilution mixed gas and the concentration of the post-dilution mixed gas, and set a diluent gas flow rate of the setting total flow rate as the diluent gas setting flow rate.

In the gas control system 200 configured as described, as illustrated in the control block diagram of FIG. 3, the concentration control mechanism 2 can perform control so as to keep the concentration of the material gas in the post-dilution mixed gas at the setting concentration, whereas the dilution control mechanism 3 can perform dilution so as to keep the total flow rate of the post-dilution mixed gas at the setting total flow rate. Accordingly, the setting total flow rate and the setting concentration can be both achieved for the post-dilution mixed gas, and therefore the post-dilution mixed gas can be supplied to the chamber in an ideal state.

Further, since in the gas control system 200, the flow rate sensor 32 is not provided in the gas supply line L2 and the concentration sensor does not contact with the material gas, even when the pre-dilution mixed gas led out of the tank T is at high temperature and/or highly reactive, important parts of the sensor, such as a light source and a light receiver, are not affected in principle. Also, droplets produced by the reliquefaction of the material gas and/or particles produced by thermal decomposition are not attached to any of the sensors respectively adapted to monitor the states of the two types of mixed gases. Accordingly, even when the flow rate or concentration of the post-dilution mixed gas is continuously controlled over a long term, the measurement accuracy of each of the sensors can be prevented from being reduced, and therefore the flow rate and concentration of the post-dilution mixed gas can be continuously kept at predetermined desired values.

In addition, as shown in Expressions (1) to (4), once the concentration $IR_{IN}$ of the pre-dilution mixed gas and the concentration $IR_{OUT}$ of the post-dilution mixed gas are known, the diluent gas setting flow rate required to achieve the setting total flow rate $Q_{TOTAL}$ can be calculated. Accordingly, even in the case where no flow rate sensor is provided in the gas supply line L2 to avoid the direct feedback control of the flow rate of the post-dilution mixed gas, by controlling the flow rate of the diluent gas to the diluent gas setting flow rate using the mass flow controller MFC provided in the diluent gas line L3, the total flow rate of the post-dilution mixed gas flowing through the gas supply line L2 can be indirectly continuously made equal to the setting total flow rate as a target.

Also, the concentration of the post-dilution mixed gas is measured by the first concentration sensor 21 to feedback-control the first valve 22 so as to follow the setting concentration. Since the first valve 22 is arranged upstream of the merging point J, and can control only the amount of the post-dilution mixed gas independently of the diluent gas, the concentration of the post-dilution mixed gas can be made follow the setting concentration while keeping a state where the total flow rate of the post-dilution mixed gas follows the setting total flow rate.

These make it possible to stably supply the post-dilution mixed gas, which is of high quality and in an ideal state where a flow rate and concentration are suitable for semiconductor manufacturing, to the chamber over a long term.

As a result, the quality of semiconductor products manufactured in the chamber can also be kept constant.

Next, a gas control system 200 according to a second embodiment of the present invention will be described.

Figure 4:
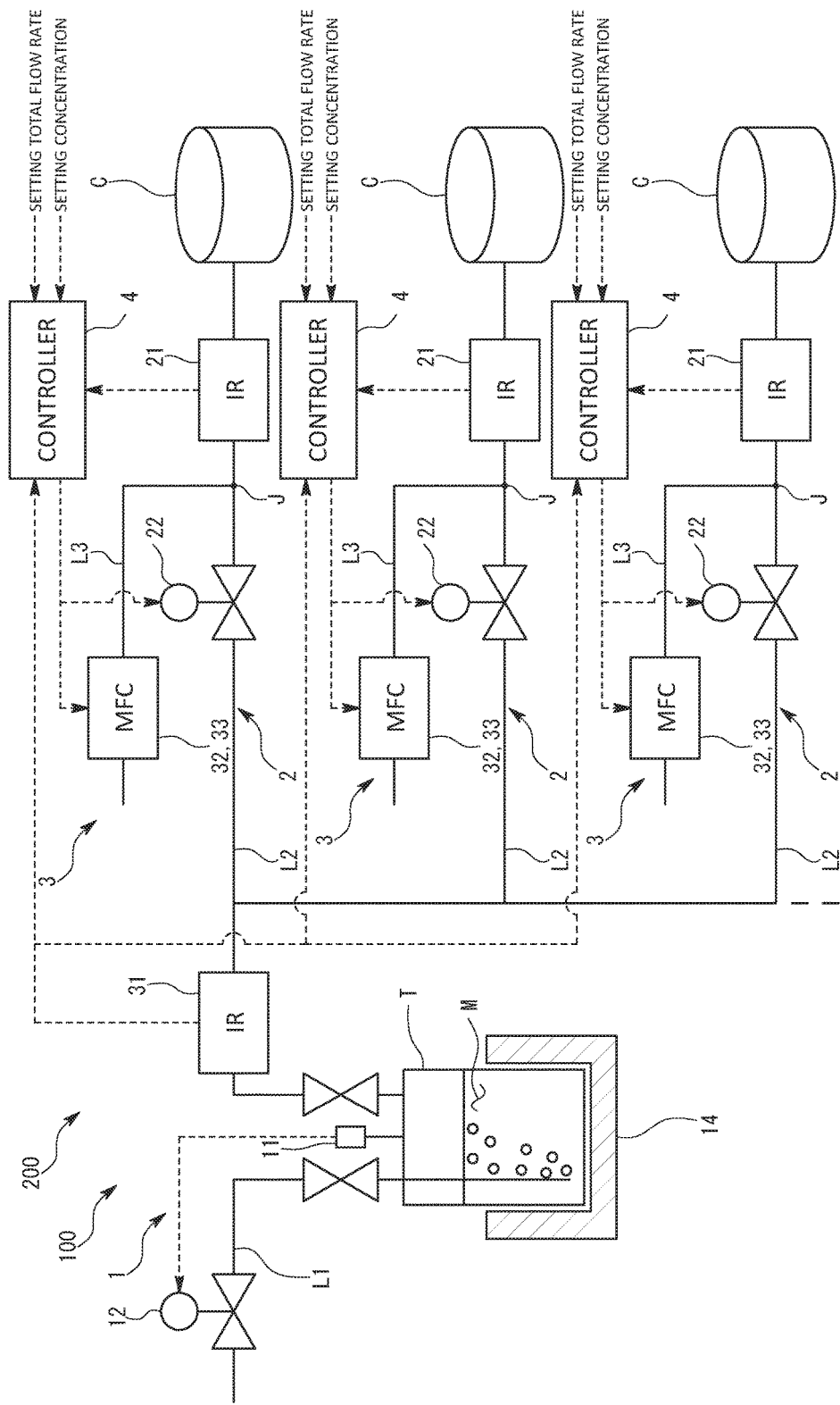
FIG. 4 is a schematic diagram illustrating a gas control system according to a second embodiment of the present invention.

The gas control system 200 of the second embodiment illustrated in FIG. 4 is one used for a vaporizer 100 configured such that multiple parallel branch gas supply lines L2 come out of one tank T, and the gas supply lines L2 are respectively provided with diluent gas lines L3.

More specifically, the n gas supply lines L2 are respectively provided with the diluent gas lines L3 one-by-one. Also, the gas supply lines L2 are respectively provided with concentration mechanisms 2 of the same type as that described in the first embodiment. Further, the diluent gas lines L3 are respectively provided with dilution control mechanisms 3 of the same type as that described in the first embodiment as well. Still further, controllers 4 are respectively provided so as to control the sets of the concentration control mechanism 2 and the dilution control mechanism 3. Note that each of the controllers 4 may implement functions thereof using one computer or may be configured using multiple computers.

Also, the pressure and temperature of the inside of the tank T are adapted to be kept constant by a material gas control mechanism 1 in the same manner as in the first embodiment to produce a material gas at a desired saturated vapor pressure.

Each of the gas supply lines L2 is adapted such that the outlet thereof is connected to introduction ports formed in mutually different places of a chamber, and thereby a post-dilution mixed gas can be uniformly introduced into the chamber. Also, the flow rate and concentration of a post-dilution mixed gas supplied through each of the gas supply lines L2 are adapted to be respectively independently controllable.

Note that a configuration for controlling the flow rate and concentration of a post-dilution mixed gas supplied through each of the gas supply lines L2 is the same as that described in the first embodiment.

As described, the gas control system 200 of the second embodiment makes it possible to, through each of the gas supply lines L2, supply a post-dilution mixed gas having a flow rate and concentration respectively independently controlled into a chamber from multiple places. Since the flow rate and concentration of a post-dilution mixed gas supplied from each of the gas supply lines L2 can be made to accurately follow a setting total flow rate and a setting concentration preset for that gas supply line L2, it becomes possible to bring a distribution state of the post-dilution mixed gas in a chamber to a state most suitable for, for example, semiconductor deposition. This is because since the post-dilution mixed gas can be introduced from multiple places, an uneven distribution of the post-dilution mixed gas in the chamber can be prevented to obtain a uniform distribution.

Next, a third embodiment of the present invention will be described.

Figure 5:
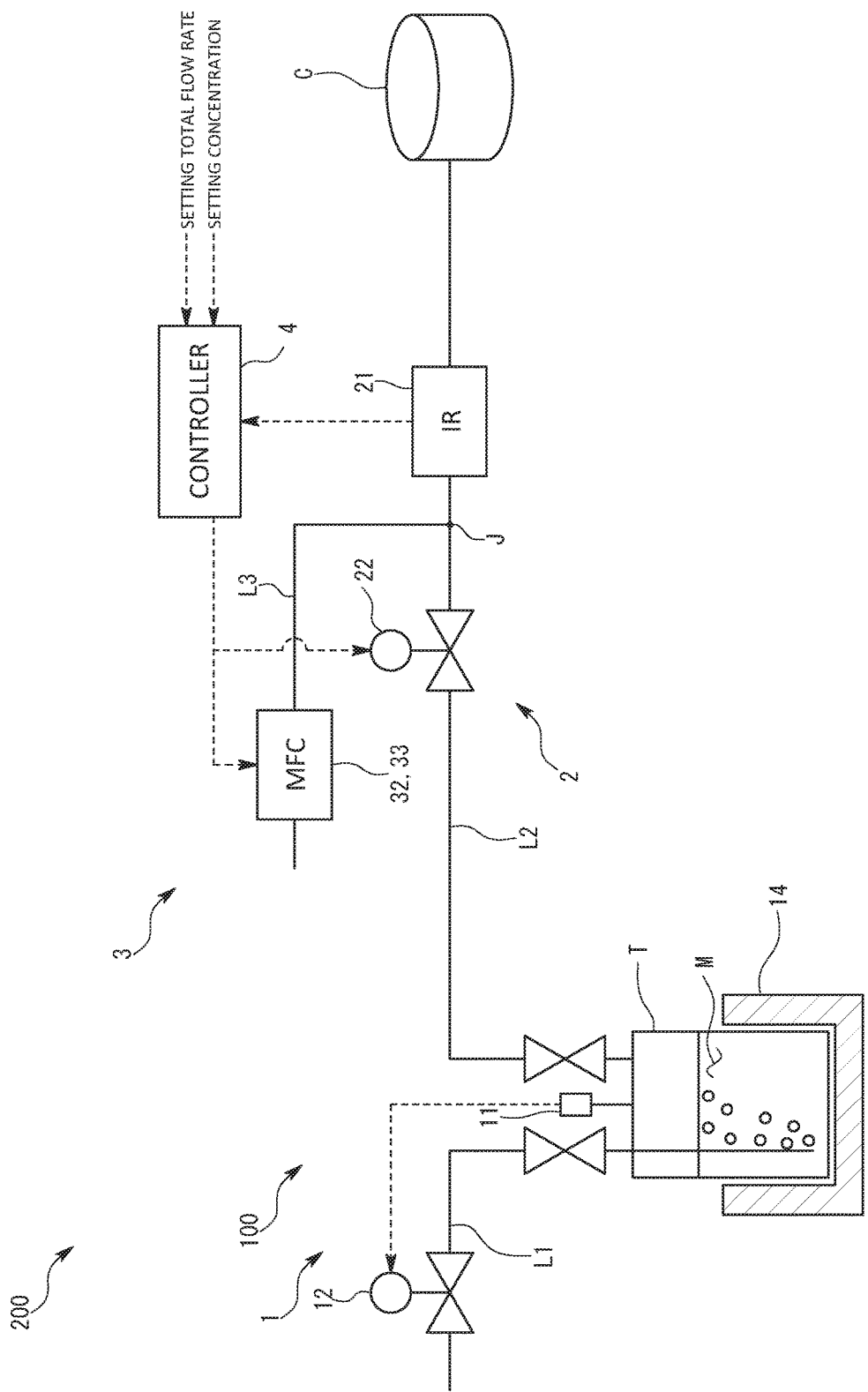
FIG. 5 is a schematic diagram illustrating a gas control system according to a third embodiment of the present invention.
Figure 6:
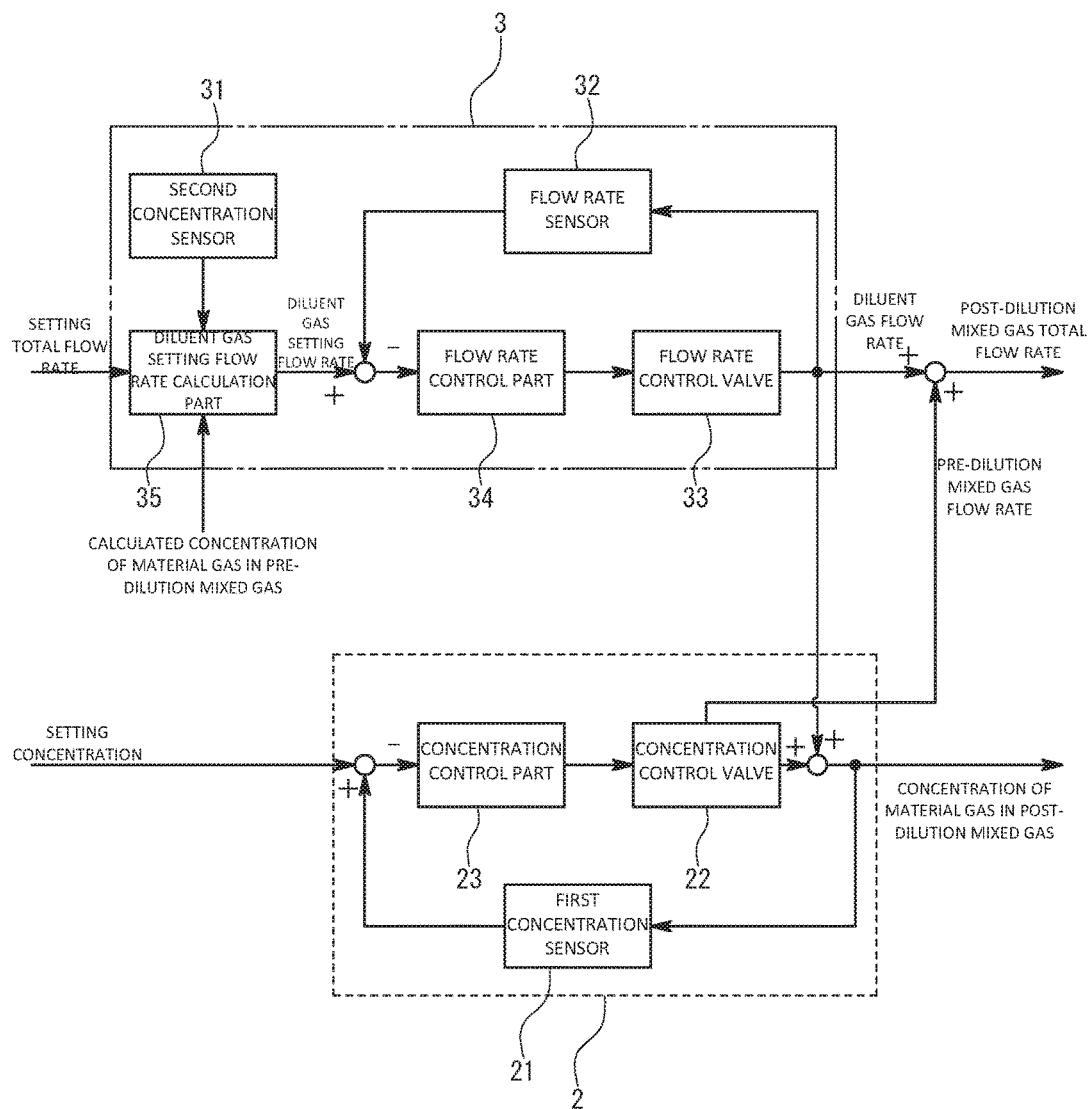
FIG. 6 is a schematic control block diagram illustrating the configurations of a concentration control mechanism and dilution control mechanism in the gas control system of the third embodiment.

As illustrated in FIGS. 5 and 6, in a gas control system 200 of the third embodiment, as compared with the gas control system 200 of the first embodiment, a diluent gas setting flow rate calculation part 35 is different in omitting the second concentration sensor 31. Also, along with the omission of the second concentration sensor 31, a use method is also different from those of the respective embodiments described above.

Specifically, in the same manner as that in the first embodiment, the diluent gas setting flow rate calculation part 35 in the third embodiment also calculates a diluent gas setting flow rate to be set at the moment on the basis of Expression (5).

[Expression 5]

$$Q_{DIL} = (1 - IR_{OUT}/IR_{IN})Q_{TOTAL} \quad (5)$$

Note that since the second concentration sensor 31 is not provided in the third embodiment, a pre-dilution measured concentration $IR_{IN}$ cannot be obtained. For this reason, the diluent gas setting flow rate calculation part 35 in the third embodiment calculates the concentration $P_S/(P_S+P_C)$ of a material gas in a pre-dilution mixed gas using the saturated vapor pressure $P_S$ of the material gas derived from the pressure and temperature of the inside of a tank T achieved by a material gas control mechanism 1 and the set supply pressure $P_C$ of a carrier gas, and uses the concentration $P_S/(P_S+P_C)$ of the material gas in place of the pre-dilution measured concentration $IR_{IN}$.

Even in such a configuration, a post-dilution measured concentration $IR_{OUT}$ measured by a first concentration sensor 21 is fed back to update the diluent gas setting flow rate appropriate for a setting total flow rate. Accordingly, the flow rate and concentration of a post-dilution mixed gas can be continuously kept at desired values.

Next, a use method for the gas control system 200 of the third embodiment will be described. In the gas control system 200 of the third embodiment, since the second concentration sensor 31 is not provided in a gas supply line L2 on an upstream side of a merging point J with a diluent gas line L3, the concentration of a pre-dilution material gas led out of the tank T is estimated on the basis of the first concentration sensor 21 and the inflow amount of a diluent gas through the diluent gas line L3. For this reason, it is necessary to check whether an estimated value of the concentration of the pre-dilution material gas is correct and whether operation is performed as expected without the occurrence of abnormality in a material gas vaporization state achieved by a temperature controller 14 and bubbling. Accordingly, in the third embodiment, before controlling the concentration of a post-dilution material gas, by fully closing a valve of a mass flow controller MFC provided in the diluent gas line L3 to prevent dilution, the material gas is made to reach the first concentration sensor 21 without being diluted, and the concentration of the pre-dilution material gas is directly measured. In this manner, whether abnormality occurs in the temperature controller 14 and/or a bubbling state is checked on the basis of whether the concentration of the pre-dilution material gas actually measured by the first concentration sensor 21 is equal to a desired concentration. When no abnormality is confirmed as a result of the check, controlling the concentration and flow rate of the post-dilution material gas is started on the basis of the above-described control rule.

Next, a fourth embodiment of the present invention will be described.

Figure 7:
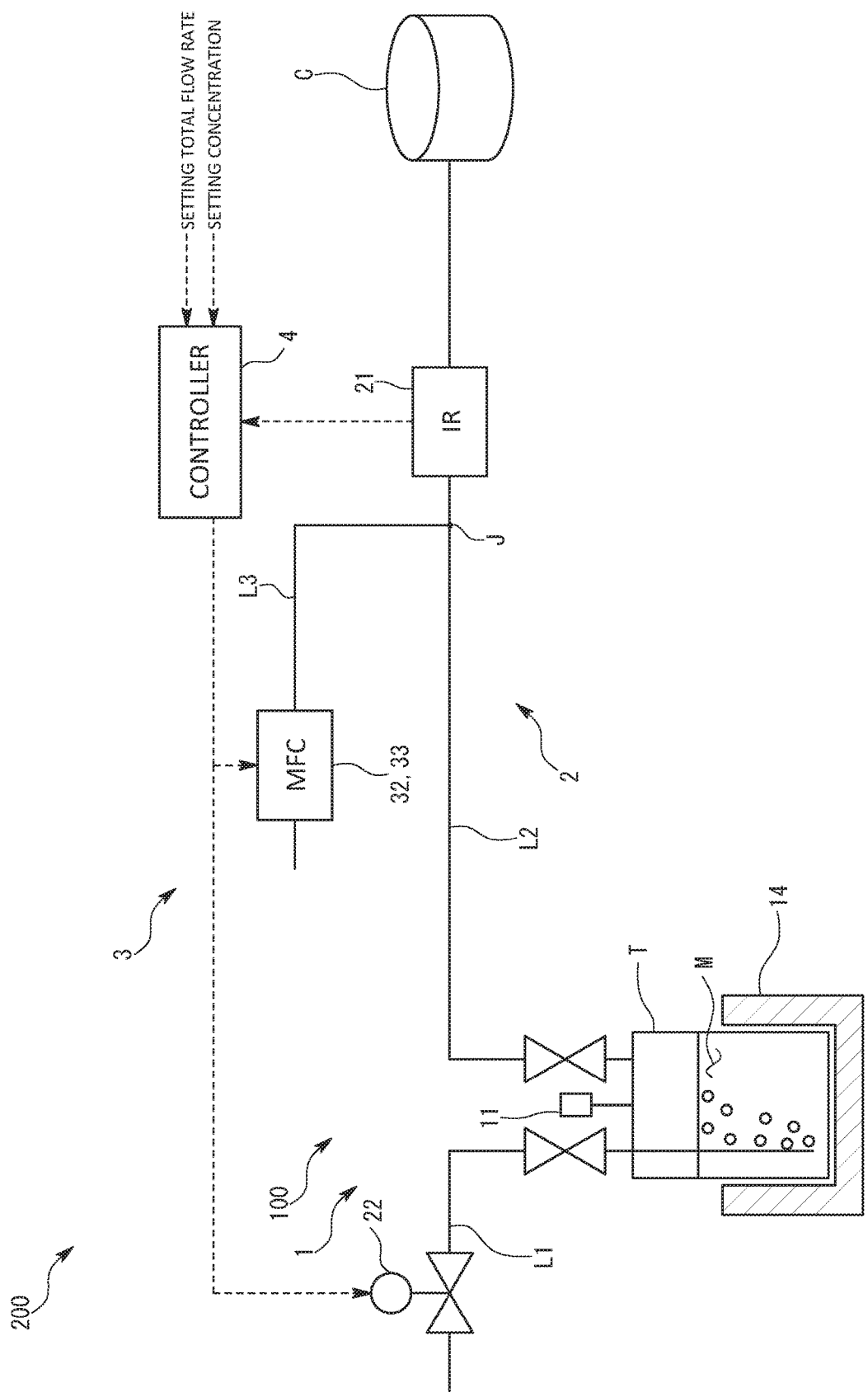
FIG. 7 is a schematic diagram illustrating a gas control system according to a fourth embodiment of the present invention.

A gas control system 200 of the fourth embodiment is different as compared with the gas control system of the third embodiment in that as illustrated in FIG. 7, a concentration control valve 22 corresponding to the first valve in the claims is provided not in a gas supply line L2 but in a carrier gas line L1. That is, no valve is present in the gas supply line L2, and a first concentration sensor 21 is also an NDIR contactless type concentration sensor, and therefore no component such as a sensor or a valve is present in a gas supply line L2 pipe. As a result, the gas supply line L2 is hollow, through which only a material gas or a diluent gas circulates, and therefore, for example, even when the material gas is a corrosive one or one likely to be condensed, any problem caused by the attachment of the material gas to a component cannot occur in principle.

Also, in the fourth embodiment, since the concentration control valve 22 is provided in the carrier gas line L1, the opening level of the concentration control valve 22 in the carrier gas line L1 is feedback-controlled on the basis of a concentration measured by the first concentration sensor 21. For this reason, the concentration control valve 22 regulates the amount of a carrier gas to be introduced into a tank T to control a state of bubbling a material M inside the tank T with the carrier gas. As a result, the amount of the material gas led out into the material gas line is controlled to an amount required to achieve the target concentration of a post-dilution material gas, and finally, the flow rate of the diluent gas through a diluent gas line L3 is controlled. As a result, the concentration and flow rate of the post-dilution material gas can be controlled to desired values.

Other embodiments will be described.

The material to be vaporized in the vaporizer is not limited to trimethyl gallium, but may be another semiconductor material. Also, the material is not limited to a liquid one, but may be a solid one.

Any of the first concentration sensor and the second concentration sensor is only required to be a contactless type sensor, but not limited to an infrared absorption type sensor. For example, an ultrasonic type concentration sensor may be used. Further, the first concentration sensor provided on the downstream side of the merging point may be a contact type concentration sensor. This is because the post-dilution mixed gas is sufficiently cooled by or diluted with the diluent gas, and even in the case of the contact type concentration sensor, the sensor is unlikely to be affected by hear or the reactivity of the material gas, and can therefore keep accuracy over a long term. As the contact type concentration sensor, it is only necessary to be one including: a total pressure sensor adapted to measure the total pressure of the post-dilution mixed gas; a partial pressure sensor adapted to measure the partial pressure of the material gas; and a concentration calculation part adapted to calculate the concentration of the material gas in the post-dilution mixed gas from the ratio between the measured total pressure and partial pressure. That is, in any of the total pressure sensor and the partial pressure sensor, a diaphragm or the like as a sensor mechanism thereof may directly contact with the post-dilution mixed gas.

In order to control the flow rate of the diluent gas in the diluent gas line, the mass flow controller is not used, but a flow rate control mechanism including a valve and a flow rate sensor, which are not packaged, may be used.

The material gas control mechanism may control only the pressure or only the temperature. Also, when constituting the gas control system of the present invention, the material gas control mechanism may be omitted.

The carrier gas flowing through the carrier gas line and the diluent gas flowing through the diluent gas line may have the same composition or different compositions. Also, the diluent gas line may be configured to branch from the carrier gas line and merge with the gas supply line so that part of the carrier gas separately flows as the diluent gas.

In order to retrofit a function as the gas control system of the present invention to an existing gas control system, the program for the gas control system described in each of the embodiments or a program storage medium storing the program may be used.

Besides, various combinations and modifications of the embodiments may be made without departing from the scope of the present invention.

REFERENCE SIGNS LIST

200: Gas control system
100: Vaporizer
L1: Carrier gas line
L2: Gas supply line
L3: Diluent gas line
T: Tank
NI: Material
1: Material gas control mechanism
11: Pressure sensor
12: Pressure control valve (third valve)
13: Pressure control part (third valve control part)
14: Temperature controller
2: Concentration control mechanism
21: First concentration sensor
22: Concentration control valve (first valve)
23: Concentration control part (first valve control part)
3: Dilution control mechanism
31: Second concentration sensor
32: Flow rate sensor
MFC: Mass flow controller
33: Flow rate control valve (second valve)
34: Flow rate control part (second valve control part)
35: Diluent gas setting flow rate calculation part

The invention claimed is:

1. A gas control system used for a vaporizer comprising: a tank adapted to contain a material; a carrier gas line adapted to introduce a carrier gas into the tank; a gas supply line through which a material gas produced by vaporizing the material and the carrier gas flow and led out of the tank; and a diluent gas line adapted to merge with the gas supply line and introduce a diluent gas into the gas supply line, the gas control system comprising:
  a first valve that is provided in the carrier gas line or provided in the gas supply line on an upstream side of a merging point with the diluent gas line;
  a flow rate control mechanism that is provided in the diluent gas line and comprises a flow rate sensor and a second valve;
  a first concentration sensor that is provided in the gas supply line on a downstream side of the merging point with the diluent gas line and adapted to measure a concentration of the material gas in a post-dilution mixed gas containing the material gas, the carrier gas, and the diluent gas;
  a first valve control part adapted to control an opening level of the first valve so as to decrease a deviation between a preset setting concentration of the material gas in the post-dilution mixed gas and a post-dilution measured concentration of the material gas in the post-dilution mixed gas, the post-dilution measured concentration being measured by the first concentration sensor;
  a diluent gas setting flow rate calculation part adapted to, on a basis of a preset setting total flow rate of the post-dilution mixed gas, the post-dilution measured concentration, and an estimated or actually measured concentration of the material gas in a pre-dilution mixed gas, calculate a diluent gas setting flow rate that is a flow rate of the diluent gas to be flowed through the diluent gas line; and a second valve control part adapted to control an opening level of the second valve so as to decrease a deviation between the diluent gas setting flow rate and a measured flow rate measured by the flow rate sensor.

2. The gas control system according to claim 1, wherein the first concentration sensor is an infrared absorption type concentration sensor.

3. The gas control system according to claim 1, further comprising
a contactless type second concentration sensor that is provided in the gas supply line on the upstream side of the merging point with the diluent gas line and adapted to measure a concentration of the material gas in the pre-dilution mixed gas containing the material gas and the carrier gas, wherein
the diluent gas setting flow rate calculation part is configured to calculate the diluent gas setting flow rate on a basis of the setting total flow rate, the post-dilution measured concentration, and a pre-dilution measured concentration of the material gas in the pre-dilution mixed gas, the pre-dilution measured concentration being measured by the second concentration sensor.

4. The gas control system according to claim 1, wherein the first valve control part is configured to, when the post-dilution measured concentration is larger than the setting concentration, change an opening level in a direction to close the first valve, and when the post-dilution measured concentration is smaller than the setting concentration, change the opening level in a direction to open the first valve.

5. The gas control system according to claim 1, further comprising:
a third valve that is provided in the carrier gas line;
a pressure sensor that is provided in the tank and adapted to measure a pressure of an inside of the tank; and
a third valve control part adapted to control an opening level of the third valve so as to decrease a deviation between a preset setting pressure and a measured pressure measured by the pressure sensor.

6. The gas control system according to claim 1, wherein:
multiple parallel branch gas supply lines are provided from the tank and diluent gas lines respectively individually merge with the gas supply lines;
the gas supply lines are respectively individually provided with first valves and first concentration sensors; and
the diluent gas lines are respectively individually provided with flow rate control mechanisms.

7. A storage medium storing a program for a gas control system used for a vaporizer comprising: a tank adapted to contain a material; a carrier gas line adapted to introduce a carrier gas into the tank; a gas supply line through which a material gas produced by vaporizing the material and the carrier gas flow and led out of the tank; and a diluent gas line adapted to merge with the gas supply line and introduce a diluent gas into the gas supply line,
the gas control system comprising: a first valve that is provided in the carrier gas line or provided in the gas supply line on an upstream side of a merging point with the diluent gas line; a flow rate control mechanism that is provided in the diluent gas line and comprises a flow rate sensor and a second valve; and a first concentration sensor that is provided in the gas supply line on a downstream side of the merging point with the diluent gas line and adapted to measure a concentration of the material gas in a post-dilution mixed gas containing the material gas, the carrier gas, and the diluent gas,
the program instructing a computer to fulfill functions as:
a first valve control part adapted to control an opening level of the first valve so as to decrease a deviation between a preset setting concentration of the material gas in the post-dilution mixed gas and a post-dilution measured concentration of the material gas in the post-dilution mixed gas, the post-dilution measured concentration being measured by the first concentration sensor;
a diluent gas setting flow rate calculation part adapted to, on a basis of a preset setting total flow rate of the post-dilution mixed gas, the post-dilution measured concentration, and an estimated or actually measured concentration of the material gas in a pre-dilution mixed gas, calculate a diluent gas setting flow rate that is a flow rate of the diluent gas to be flowed through the diluent gas line; and
a second valve control part adapted to control an opening level of the second valve so as to decrease a deviation between the diluent gas setting flow rate and a measured flow rate measured by the flow rate sensor.

* * * * *